United States Patent [19]

Garito et al.

[11] 4,433,960
[45] Feb. 28, 1984

[54] EXTRACORONAL DENTAL SPLINT AND SPLINTING METHOD

[76] Inventors: Jon C. Garito, 22 Deering La., East Rockaway, N.Y. 11558; Alan G. Ellman, 1 Auerbach La., Lawrence, N.Y. 11516

[21] Appl. No.: 501,054

[22] Filed: Jun. 9, 1983

Related U.S. Application Data

[63] Continuation of Ser. No. 282,942, Jul. 13, 1981, abandoned.

[51] Int. Cl.³ .................................................. A61C 5/00
[52] U.S. Cl. ........................................ 433/215; 433/9; 433/180
[58] Field of Search ................... 433/1, 9, 43, 45, 172, 433/180, 215, 225, 229; 128/89 R

[56] References Cited

U.S. PATENT DOCUMENTS

| | | | |
|---|---|---|---|
| 713,273 | 11/1902 | Alexander | 433/40 |
| 3,249,109 | 5/1966 | Maeth et al. | 433/180 |
| 3,487,545 | 1/1970 | Weissman | 433/215 |
| 4,015,334 | 4/1977 | Moss | 433/17 |
| 4,165,561 | 8/1979 | Miller et al. | 433/9 |
| 4,172,323 | 10/1979 | Orlowski | 433/180 |
| 4,204,325 | 5/1980 | Kaelble | 433/9 |
| 4,213,452 | 7/1980 | Shippert | 128/89 R |
| 4,360,342 | 11/1982 | Salvo | 433/172 |

OTHER PUBLICATIONS

"Metal-Reinforced Anterior Tooth Replacement Using Acid-Etch Composite Resin Technique", by Nathanson et al.-Apr. 1980.

Primary Examiner—Gene Mancene
Assistant Examiner—David I. Tarnoff

[57] ABSTRACT

A novel extracoronal dental splint and procedure comprises a thin, flat, slightly malleable perforated strip or mesh which is adhered to the patient's inner dental arch and then covered with a thin layer of resin or composite material, which when hardened firmly bonds the strip to the patient's teeth stabilizing any mobile teeth.

11 Claims, 7 Drawing Figures

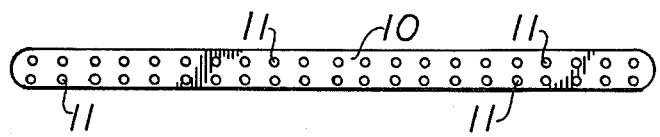
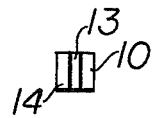
FIG. 1    FIG. 2
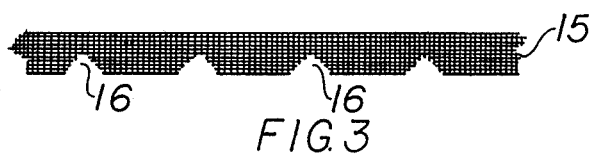
FIG. 3
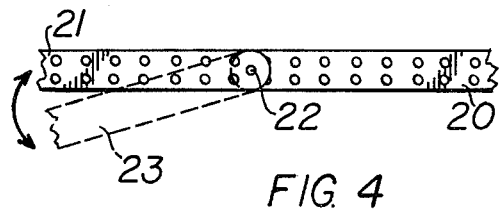
FIG. 4
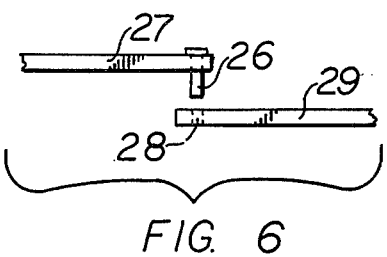
FIG. 5    FIG. 6
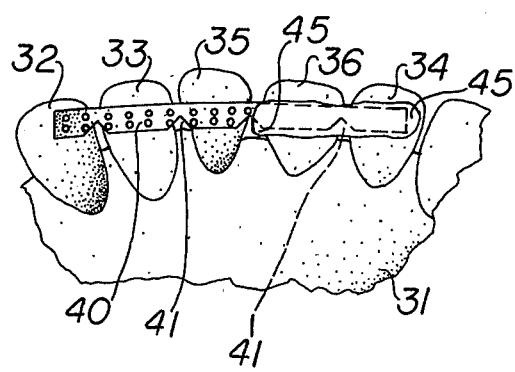
FIG. 7

EXTRACORONAL DENTAL SPLINT AND SPLINTING METHOD

This is a continuation of application Ser. No. 282,942, filed July 13, 1981, which is now abandoned.

This invention relates to a novel dental splint and novel splinting procedure for stabilizing one or more human or animal teeth by joining it to another tooth.

Temporary or semi-permanent splinting of mobile teeth, sometimes called periodontal splinting, provides relief for patients whose mobile teeth interfere with comfort or function, where retention is needed to prevent tooth migration, and in circumstances where health, age, or cost rule out relatively traumatic or lengthy restorative procedures or conventional fixed prosthetic devices. Both extracoronal (external to the natural tooth) and intracoronal (inside the natural tooth) splinting are known using a variety of materials.

The known intracoronal splinting includes amalgam splints, the placement of twisted wire, orthodontic wire, screws, and bars drilled into virgin teeth or into previously placed amalgams. The teeth or restorations within the teeth are grooved, either occlusally, circumferentially or incisally, and the various wires, pins, or bars are then fixed within these grooves with amalgam, self-polymerizing resins or composites. The disadvantages of intracoronal splinting is it is irreversible and requires the patient to make a firm commitment to (a) permanent restorative procedures in the future or (b) constant maintenance of the splint at regular intervals. Also intracoronal splints, due to caries following the fracture or leakage of the material utilized, often results in gross mutilation of the teeth.

The known extracoronal splinting includes wire ligation, plastic reinforced wire splints, bar wire acrylic splints, bands welded together, removable acrylic and cast appliances, and more recently the self-polymerizing resins and composites with enamel etchants, used alone or incorporating ligature wire or cast forms. The disadvantages of the extracoronal splint, though it has the advantage of preserving natural tooth structure, is that it is not esthetically pleasing due to excessive bulk of resins or composites, wires showing through the resin or composite material; and the staining of these materials. When the composites or resins are used alone, there is often fracturing or shearing of the material interproximally. In many patients with special problems, e.g., mouth breathers, thumbsuckers, those with tongue habits and those who bite nails or other foreign objects, the materials tend to stain, or flake away even more easily.

The principal objects of the invention are new procedures and devices for extracoronal stabilization that combines the advantages of preserving natural tooth structure with the advantage of an inexpensive, esthetic, easy to construct splint, which considerably reduces chairside time, and results in more productivity for the dentist, less time and trauma suffered by the patient, and significantly reduced expense to the patient.

Briefly speaking, in accordance with the present invention, the novel splint is a thin, flat, slightly flexible or malleable strip of grid-like material, such as a mesh or perforated strip. The strip has sufficient strength to stabilize the mobile teeth, yet during installation remains sufficiently flexible so as to be bendable by the dentist to conform to the teeth curvature.

Preferably, the strip is provided with a pressure-sensitive adhesive backing to allow it to adhere to the surface of the inner curvature of the teeth and arch on natural dentition or stone models.

In use, the dentist, after adjusting its length and if desired adding small V-slots at the interproximal areas, would adhere the strip to the patient's teeth, and then spread a thin layer of known resin or composite over the adhered strip and around its edges. The resin or composite enters the holes or openings in the strip and upon hardening solidly bonds the strip to the teeth to form a rigid bond joining the contacted teeth to one another.

The invention will now be described in greater detail with reference to several exemplary embodiments of the invention taken in conjunction with the accompanying drawings, wherein:

FIG. 1 is a plan view of one embodiment of a splinting device in accordance with the invention, of the perforated strip type;

FIG. 2 is an end view of the device of FIG. 1;

FIG. 3 is a plan view of a second embodiment of splinting device in accordance with the invention, of the woven mesh type;

FIG. 4 is a plan view of a third embodiment of a splinting device in accordance with the invention, which is of the double hinged strip type;

FIG. 5 is a side view of the device of FIG. 4;

FIG. 6 is a side view of a modification of the device of FIG. 5;

FIG. 7 is an inside view of part of a patient's dental arch showing on the left the adhered strip of the embodiment of FIG. 1, and on the right the partial addition of a layer of resin or composite material over the adhered strip.

The splinting device of the invention is a thin flat strip of mesh or perforated metal which has stiffness but is slightly malleable or flexible to allow bending to conform to the inner curvature of the teeth or arch. The strip if of metal may be made of non-corrosive materials such as brass, stainless steel or titanium, and if of non-metal of fiberglass, nylon or other plastic resins. It can be a perforated solid strip, or a woven mesh. The width should be about 2-4 mm wide and of sufficient length to encompass a full dental arch, typically 3 inches. A typical thickness is about 1/32 inches. The strip is preferably provided on one flat side with a thin layer of known pressure-sensitive adhesive that will adhere to the teeth. The adhesive can be covered with a removable separator, such as a paper backing, to allow ready handling by the dentist prior to adherence to the teeth.

FIG. 1 is a plan view of a perforated metal or resin strip 10 in accordance with one embodiment of the invention. Preferably, there are 15-20 holes 11 per inch. The strips 10 are readily formed by cutting or slicing from a larger perforated sheet. While the edge cuts are shown as extending between the rows of perforations, this is not essential, and the cuts can be made along the row of perforations, with the result that the strip would have one row of holes along the center, and two rows of partial holes along each outer edge. The strip ends can be rounded as shown, or cut straight across. The backside of the strip is preferably provided with a thin layer 13 of known pressure-sensitive adhesive, to which is attached a thin removable separating layer 14, for example, of paper, to preserve the adhesive before use, as illustrated in FIG. 2.

FIG. 3 illustrates on a somewhat enlarged scale a woven mesh strip 15 of nylon fibers in accordance with the invention. In this case, small V-slots 16 have been precut along the bottom edge. The spacing of the V-slots 16 is to approximate the interproximal areas of the dental arch. The dentist can be provided with a kit of strips with different V-slot spacings for different patients. The presence of the V-slots 16 enables the flat surface of the strip to be bent along the inciso-gingival dimension, so that when the strip is bonded to the tooth, the V-slots allows access by the patient or the dentist to the interproximal spaces for cleaning purposes. The strips need not be precut with the V-slots, but can be sold to the dentist with the edges intact, and then the dentist can readily cut the V-slots 16 where needed while fitting the device to the patient. While the adhesive backing 13 is preferred for simplifying use by the dentist, the strips can be supplied without adhesive to the dentist, who after fitting the strip 10, would then apply to the strip back any known fast-drying tooth adhesive layer.

As mentioned, the strip 10 or 15 must be malleable and thus bendable perpendicular to the plane of the strip so it can be caused to follow the inner curvature of the dental arch. Since the dental arch may also be higher or lower in posterior, ie., at the rear, some malleability or bendability in the plane of the strip may prove useful. Such an embodiment is disclosed in FIGS. 4 and 5. In this embodiment, the strip is composed of two similar segments or parts 20 and 21 hinged together at their adjacent ends by a pin 22. This would allow some lateral movement, as shown in dash-dot lines at 23 in FIG. 4, of one of the parts 21 with respect to the other part 20 so that the fit to the patient's dental arch can be improved or properly adjusted. The two strip parts 20, 21 can be pinned at the factory and sold pre-pinned to the dentist, or extra holes provided at the ends as shown and a supply of loose pins included in a kit to the dentist who could then use as needed, or, as a further alternative as shown in FIG. 6, a pin 26 may be connected to one hole 28 at the end of each strip part 27. In the latter case, the dentist when needed would fit it into the hole 28 on the other strip part 29 and peen over, brad, or rivet in place during fitting to the patient. If not needed, the dentist need merely cut off the pin end. If loose pins are supplied, the dentist could pin the two strip parts together by similar techniques as needed. The adhesive should be removed, as by scraping or guiding, where the two strip parts overlap to allow movement of the hinged section.

The splinting procedure according to the invention is as follows. Preferably the dentist first prepares a diagnostic model of the patient's dental arch containing the mobile tooth or teeth. He then chooses a splint of one of the types described above and fits it to the inside of the dental arch along the inside surfaces of the teeth. Preferably, the strip should overlie at least one tooth on each side of the mobile tooth to be stabilized. The dentist then cuts the strip to the proper length using ordinary or metal cutting scissors, and then fits the V-slots to the interproximal areas, or cuts V-slots in the strip edge as previously described so the slots overlie the interproximal areas. Next, the dentist removes the paper backing and presses the adhesive side of the strip along the patient's dental arch with the V-slots located in the proper areas. A suitable tool can be used to press the strip against the tooth sides along the spaces between adjacent teeth. The strip will adhere to the teeth and remain in position, during the subsequent steps of this procedure. If desired, the patient's teeth inner surface may be subjected in an earlier step to a known enamel etching treatment to improve adherence of the resin or composite soon to be added.

The dentist then chooses one of many well-known tooth adherent hardenable resins or composites that are available or can be prepared as a cream, paste or ointment. Typical composite examples are, for example, Johnson & Johnson "Adaptic", Caulks "Nuvoseal" or cold-cured resins such as Ellman's "Cyanoveneer". The dentist then spreads the resin or composite over the adhered strip so that it covers the strip, fills or oozes into the strip openings, and contacts the tooth surfaces through the openings and along the long and short edges of the strip. The excess resin or composite is quickly removed and the material left is brushed and smoothed over the entire strip surface and edges evenly and thinly. Most of those materials set quickly, in about 5 minutes. No holding forces or forms are necessary, as the strip remains adhered or fixed to the tooth surfaces during the setting process. When the material, resin or composite, has hardened, the strip is firmly bonded to the teeth and stiff reinforcing solid splint is formed along the inner dental arch which stabilizes any mobile teeth to which the strip is bonded.

FIG. 7 is a schematic view of the inner arch of several teeth of a patient embedded in the gum 31. It is assumed that the end teeth 32, 33 and 34 are stable, but the inner teeth 35 and 36 are mobile and need to be stabilized. The left side of FIG. 7 shows a strip 40 of the type of FIG. 1 having V-slots 41 provided at the interproximal areas at the gum 31 line. The right side of FIG. 7 shows a partial layer 45 of resin or composite that has been spread by the dentist over the adhered strip. To complete the procedure, the resin or composite material 45 would be spread over the entire strip as above described.

As an alternative procedure, for use when a tooth is missing, the strip can be bent completely around the distal of the distal tooth in the segment to be splinted. The buccal and lingual ends of the strip when brought together on the mesial surface of the isolated distal tooth become bonded together by the adhesive backing. The strip can then be carried over and adhered to the remaining teeth as previously described. The composite or resin when added is applied not only over the strip parts adhered to the tooth surfaces, but also over the strip part bridging the empty space to stiffen same after hardening. It should also be possible to place a tooth in the empty space to be held and fixed in place by the strip bridging the gap.

There are many advantages of the invention over the known splinting devices and procedures. These include the following:

a. The natural tooth structure is preserved;
b. The splint is inexpensive and easy to fit and apply to the patient;
c. Chairside time is reduced resulting in more productivity for the dentist and less expense to the patient;
d. Little trauma is suffered by the patient;
e. The resultant splint is on the inside arch and has little bulk or thickness and is thus less visible, and moreover with the use of properly tinted resins or composites a further improvement in visibility results. Thus, it is esthetically pleasing to the patient.
f. Due to provision of the V-slots, the embrasure space between adjacent teeth remains free and accessible for cleansing.
g. The smoothed resin or composite over the inner surface causes less discomfort to the patient. It will also smoothly cover the hinged joint of the FIG. 4 embodiment.

While the holes or perforations 11 as shown in the splint are circular, it is understood that any geometrical shape that will allow the resin or composite to flow through can be used. Moreover, it will further be apparent that the holes need not be aligned in rows but could be randomly distributed over the strip. In addition, while V-slots are shown along one edge, it will be apparent that V-slots can be provided along both long edges to increase accessibility to the spaces between teeth for cleansing. Still further, while the preferred embodiment has an adhesive layer on only one splint side, an adhesive layer can be applied on both sides. This would have particular advantage for the alternative procedure described above, when the strip is wrapped around a tooth or in a modified procedure woven in and out among the teeth to strengthen the reinforcement, in which cases both adhesive sides can contribute to holding the strip to the teeth. The resin or composite will stick to the adhesive, and, of course, to the teeth through the strip holes.

As above mentioned, the materials needed to carry out the procedure can be made available to the dentist in kit form. The kit can conveniently include a number of strips, some with adhesive on one side, some with adhesive on both sides, a supply of the resin or composite to be used in the procedure after the strip has been fitted to the patient's teeth, and can also include hinged strips as illustrated in FIG. 5, or unconnected strips with rivets for attaching two strips together, as illustrated in FIG. 6. In the latter case, a hand-riveting tool can be included in the kit for forming the riveted connection. In addition, a hand punch can be provided in the kit, the punch having, for example, a top male die configured as a triangle, and a mating bottom female die with a generally triangular opening, to enable ready punching of the V-slots by the dentist where desired.

While our invention has been described in connection with specific embodiments thereof, those skilled in the art will recognize that various modifications are possible within the principles enunciated herein and thus the present invention is not to be limited to the specific embodiments disclosed.

What is claimed is:

1. An extracoronal dental splint comprising a thin, flat, perforated strip, said strip being substantially straight and elongated in a longitudinal direction and having a width dimension in the plane of the strip and a thickness direction perpendicular to the plane of the strip, said strip having a width substantially smaller than its length and a thickness substantially smaller than its width and being slightly malleable in its thickness direction, thereby adapting the strip to be bent and fitted against the uncut inner dental arch, said perforations being sufficiently large to allow passage of a dental adhesive, said strip comprising two strip segments with a hinged connection connecting their ends allowing flexing in the strip plane.

2. A dental splint as claimed in claim 1, wherein the strip is a thin woven flexible mesh of metal or plastic resin and cutable by scissors.

3. An extracoronal dental splint as claimed in claim 1 and further comprising a thin layer of pressure-sensitive adhesive on one side of said strip.

4. A dental splint as claimed in claim 3 and further comprising a separating layer on the adhesive layer.

5. An extracoronal dental splint as claimed in claim 2 wherein the strip contains rows of perforations.

6. A dental splint as claimed in claim 1 and comprising a pin mounted at one end of the strip.

7. An extracoronal dental splinting procedure for immobilizing one or more intermediate mobile teeth in a continuous row of at least four teeth without any missing teeth and with at least the end teeth being immobile, comprising the steps of:
 a. providing a thin flat substantially straight slightly malleable strip having holes therein and having a length sufficient to span the entire row,
 b. without cutting or drilling any of the teeth, fitting the strip to the lingual surfaces of an inner dental arch of the patient so as to overlie the row of at least four teeth including the end immobile teeth and at least one intermediate mobile tooth,
 c. without cutting or drilling any of the teeth, applying the strip to the said inner dental arch defined in step b,
 d. while holding the strip against the inner dental arch, smoothing a hardenable creamy-type resin or composite material over the entire held strip so as to fill the holes therein and contact the tooth surfaces against which the strip is held, and
 e. while still retaining the strip against the inner dental arch, allowing the hardenable material to harden firmly bonding the strip to the said row of immobile and mobile teeth along the inner dental arch and stiffening the strip to stabilize the mobile tooth.

8. A dental splinting procedure as claimed in claim 7 wherein the strip is a woven mesh.

9. A dental splinting procedure as claimed in claim 7 wherein the strip is of metal or plastic resin, and is about 2–4 mm wide and 1/32 inches thick.

10. A dental splinting procedure as claimed in claim 7 wherein a series of spaced V-slots are provided along one long edge of the strip.

11. An extracoronal dental splinting procedure as claimed in claim 7 wherein the strip has an adhesive backing and spaced V-slots along one long edge, step b is carried out so as to position the V-slots over the interproximal areas, step c is carried out by pressing the adhesive backed strip over the teeth along the inner dental arch, and step d is carried out by smoothing excess material over the exposed surface of the strip.

* * * * *